(12) United States Patent
Dhurandhar et al.

(10) Patent No.: US 9,220,437 B2
(45) Date of Patent: Dec. 29, 2015

(54) DIAGNOSTIC CLASSIFICATIONS OF PULSE SIGNAL WAVEFORM DATA

(75) Inventors: Medha Sanjeev Dhurandhar, Pune (IN); Girish Shrikrishna Tillu, Pune (IN)

(73) Assignee: CENTRE FOR DEVELOPMENT OF ADVANCED COMPUTING, Pune (IN)

( * ) Notice: Subject to any disclaimer, the term of this patent is extended or adjusted under 35 U.S.C. 154(b) by 534 days.

(21) Appl. No.: 13/256,568

(22) PCT Filed: Jul. 23, 2010

(86) PCT No.: PCT/IB2010/001812
§ 371 (c)(1),
(2), (4) Date: Sep. 14, 2011

(87) PCT Pub. No.: WO2011/141765
PCT Pub. Date: Nov. 17, 2011

(65) Prior Publication Data
US 2012/0184861 A1    Jul. 19, 2012

(30) Foreign Application Priority Data

May 14, 2010 (IN) .................. 1542/MUM/2010

(51) Int. Cl.
*A61B 5/02* (2006.01)
*A61B 5/053* (2006.01)
(Continued)

(52) U.S. Cl.
CPC ............ *A61B 5/0535* (2013.01); *A61B 5/0205* (2013.01); *A61B 5/02007* (2013.01);
(Continued)

(58) Field of Classification Search
CPC .... A61B 5/021; A61B 5/024; A61B 5/02438; A61B 5/026; A61B 5/028; A61B 5/0535; A61B 5/022

USPC .................................................. 600/500–501
See application file for complete search history.

(56) References Cited

U.S. PATENT DOCUMENTS 5,533,511 A * 7/1996 Kaspari et al. ................ 600/485
6,261,235 B1    7/2001 Amano et al.
(Continued)

FOREIGN PATENT DOCUMENTS

CN    1305766    8/2001
CN    1537508    10/2004
(Continued)

OTHER PUBLICATIONS

"Increased augmentation index and systolic stress in type 1 diabetes mellitus" by Wilkinson et al., QJ Med, V.93, pp. 441-448, 2000.*
(Continued)

*Primary Examiner* — Patricia Mallari
*Assistant Examiner* — Vasuda Ramachandran
(74) *Attorney, Agent, or Firm* — Foley & Lardner LLP

(57) ABSTRACT

Diagnostic classifications of pulse signal waveform data is provided. In one example, diagnosis or prediction of a disease may be performed by analyzing pulse signal waveform data, and comparing aspects of the pulse signal waveform data with a morphology pattern that has been found to indicate a subject is suffering from a specific disease. A pulse signal can be captured via wrist electrodes using bio-electric sensors based on an impedance plethysmographic principle, for example, and processed using feature extraction for diagnosis and assessment of the subject's proneness to a disease. Analysis of the pulse signal and pulse morphology patterns provides an in-vitro, non-invasive, and low-cost method for diagnosing diseases.

19 Claims, 14 Drawing Sheets

(51) Int. Cl.
- A61B 5/0205 (2006.01)
- A61B 5/0245 (2006.01)
- A61B 5/00 (2006.01)

(52) U.S. Cl.
CPC .............. *A61B5/0245* (2013.01); *A61B 5/681* (2013.01); *A61B 5/6824* (2013.01); *A61B 5/7264* (2013.01); *A61B 5/7257* (2013.01)

(56) References Cited

U.S. PATENT DOCUMENTS

| | | | |
|---|---|---|---|
| 6,955,652 | B1 | 10/2005 | Baum et al. |
| 2002/0045808 | A1* | 4/2002 | Ford et al. ................... 600/347 |
| 2003/0163032 | A1* | 8/2003 | Terry ........................... 600/322 |
| 2006/0178585 | A1 | 8/2006 | Sharrock |
| 2007/0156036 | A1 | 7/2007 | Pilon et al. |
| 2007/0156063 | A1 | 7/2007 | Zoth et al. |

FOREIGN PATENT DOCUMENTS

| | | |
|---|---|---|
| CN | 1935084 | 3/2007 |
| EP | 0 968 681 | 1/2000 |
| JP | 2000-217796 | 8/2000 |
| WO | WO-2008/132751 | 11/2008 |

OTHER PUBLICATIONS

Moran, "Pulse", Clinical Medicine, III Edition, Butterworth Publishers, 1990, pp. 98-100.

Vlachopoulos, et al., "Genesis of the Normal and Abnormal Arterial Pulse", Current Problems in Cardiology, 2000, 25:301-367.

Babu, et al., "Impedance Plethysmography: basic priniciples", J. Postgrad Med 1990, 36:57-63.

Megnien, et al., "Comparative effects of diabetes mellitus and hypertension on physical properties of human large arteries", J. Am Coll Cardiol, 1992, 20:1562-68.

Tajaddini, et al., "Impact of age and hyperglycemia on the mechanical behavior of intact human coronary arteries: an ex vivo intravascular ulstrasound study", Am J. Physiol Hear Circ Physiol, 2005, 288: 250-255.

Woolam, et al., "The Pulse Wave Velocity as an Early Indicator of Atherosclerosis in Diabetic Subjects", Circulation, 1962, 25, 533-539.

Nurnberger, "Augmentation index is associated cardiovascular risk", J. Hypertens, 2002, 20(12):2337-40.

Dart, et al., "Pulse pressure—a review of mechanisms and clinical relevance", J. Am. Coll. Cardiol., 2001, 37: 975-984.

Ghaffar, et al., "Burden of non-communicable diseases in South Asia", BMJ, 328, 807-810, International Diabetes Federation, Apr. 3, 2004.

Diabetes altas 2000. Brussels: IDF, 2000, http://www.diabetesatlas.org/content/background-papers-pdf.

Wilkinson,et al., "Increased augmentation index and systolic stress in type 1 diabetes mellitus", Q J Med 2000, vol. 93, pp. 441-448.

Woodman, et al., "Measurement and application of arterial stiffness in clinical research: focus on new methodologies and diabetes mellitus", Med Sci Monit, 2003, vol. 9, pp. RA81-RA89.

Brooks, et al., "Augmentation of Central Arterial Pressure in Type 1 Diabetes", Diabetes Care, 1999, vol. 22, pp. 1722-1727.

Nichols, Clinical Measurement of Arterial Stiffness Obtained from Noninvasive Pressure Waveforms, American Journal of Hypertension, 2005, vol. 18, pp. 3S-10S.

Millasseu, et al., "Determination of age-related increases in large artery stiffness by digital pulse contour analysis", Clinical Science, 2002, vol. 103, pp. 371-377.

International Search Report and Written Opinion prepared by the Australian Patent Office in International Application No. PCT/IB2010/001812, mailed Nov. 23, 2010.

Miyai et al., "Noninvasive assessment of arterial distensibility in adolescents using the second derivative of photopplethysmogram waveform", European Journal of Applied Physiology, 2001, vol. 86, No. 2 pp. 119-124.

Ping, et al., "A novel method for diabetes diagnosis based on electronic nose", Biosensors & Bioelectronics, vol. 12, No. (9-10), pp. 1031-1036 (1997).

Supplementary European Search Report for EP Application No. 10851327 dated Aug. 4, 2014.

Wang, L. et al., "An Acetone Nanosensor for Non-invasive Diabetes Detection," Proceedings of the 13th International Symposium on Olfaction and Electronic Nose. AIP Conference Proceedings, vol. 1137, pp. 206-208 (2009).

* cited by examiner

1. $X < \min\{A, Y'\}$; and
2. $(A-X) > (\alpha X/100)$ where $\alpha$ is a constant $X = Y' = Z$

DIAGNOSTIC CLASSIFICATIONS OF PULSE SIGNAL WAVEFORM DATA

CROSS REFERENCE TO RELATED APPLICATION

The present application is a U.S. National Phase Application pursuant to 35 U.S.C. 371 of International Application No. PCT/IB2010/001812, filed on Jul. 23, 2010, which claims priority to a corresponding patent application filed in India and having application number 1542/MUM/2010, filed on May 14, 2010, the entire contents of which are herein incorporated by reference.

BACKGROUND

A pulsating sensation of blood vessels (generally arteries) due to ejection of blood by a heart (or machine) is known as a pulse. The Pulse is an abrupt expansion of an artery resulting from a sudden ejection of blood and transmission of the blood throughout an arterial system. A left ventricle of the heart contracts and ejects blood into the aorta, which carries the blood bolus through branches of peripheral arteries to various organs and tissues. The arterial pulse perceived by a clinician is the pressure pulse in a large, accessible artery. Generally, a pulse can be examined at sites such as radial, carotid, subclavian, brachial, femoral popliteal, posterior tibial, dorsalis pedis etc., and in clinical practice, a common pulse examination site is a radial artery.

Pulse is related to various events of left ventricle, aorta, and peripheral arteries, and hence the pulse reflects a status of related organs. A common application of pulse'examination is a measurement of heart beats as each pulsation is a result of a ventricular systole. An absence of a pulse may suggest occlusion by a thrombus or dissection, and a diminished pulse may relate to vascular pathology or impairment of a cardiac function, for example. A low volume and amplitude (hypokinetic) pulse is found in low cardiac output while a high volume and amplitude (hyperkinetic) pulse is a sign of anxiety, exercise, fever hyperthyroidism, and anaemia, for example.

Pulse is also studied with other functions and events (e.g., inspiration and expiration related changes as pulsus paradoxus). Pulse changes according to various factors such as age, time; disease state (e.g., increases in fever), ongoing treatment, etc., and these aspects help physicians diagnose a patient. Thus, pulse examination may also be helpful in evaluation of drug response and patient monitoring.

There are various invasive and noninvasive methods to study blood flow through arteries. Invasive methods include insertion of a catheter to study blood flow in arteries. Noninvasive techniques include doppler ultrasonic probe, pressure sensors, and impedance plethysmography, (e.g., determining changing tissue volumes in the body based on a measurement of electric impedance at a body surface).

Pulse examination based research currently aims at cardiovascular health, identification of risk factors and early detection of diseases.

SUMMARY

In one example aspect, a method of making diagnostic classifications of pulse signal waveform data is provided that includes receiving pulse signal waveform data, identifying systolic peak data points in the pulse signal waveform data corresponding to a systolic peak indicating a heart beat, and based on the systolic peak data points, identifying complexes in the pulse signal waveform data. A complex comprises a sub-waveform in the pulse signal waveform data approximately between an on-set data point and an off-set data point, and each complex includes deflection data points between the on-set point and the off-set point. One of the deflection data points is a systolic peak corresponding to a heart beat. The method further includes determining a pattern distribution of the complexes that indicates a frequency of pulse patterns appearing in the complexes of the pulse signal waveform data. The method further includes based on the pattern distribution, making a diagnostic classification of the pulse signal waveform data.

In another example aspect, a computer readable medium having stored therein instructions executable by a computing device to cause the computing device to perform functions is provided. The functions include receiving, pulse signal waveform data, identifying systolic peak data points in the pulse signal waveform data corresponding to a systolic peak indicating a heart beat, and based on the systolic peak data points, identifying complexes in the pulse signal waveform data. A complex comprises a sub-waveform in the pulse signal waveform data approximately between an on-set data point and an off-set data point, and each complex includes deflection data points between the on-set point and the off-set point. One of the deflection data points is a systolic peak corresponding to a heart beat. The method also includes determining a pattern distribution of the complexes that indicates a frequency of pulse patterns appearing in the complexes of the pulse signal waveform data, and based on the pattern distribution, making a diagnostic classification of the pulse signal waveform data.

In still another example aspect, a system is provided that includes a database storing known patterns of pulse signals, an input interface for receiving pulse signal waveform data, and a processor for identifying systolic peak data points in the pulse signal waveform data corresponding to a systolic peak indicating a heart beat. The processor further based on the systolic peak data points identifies complexes in the pulse signal waveform data that comprise a sub-waveform in the pulse signal waveform data approximately between an on-set data point and an off-set data point. Each complex includes deflection data points between the on-set point and the off-set point, and one of the deflection data points is a systolic peak corresponding to a heart beat. Using the deflection data points the processor compares a pattern of each complex with the known patterns of pulse signals in the database, and makes a diagnostic classification of the pulse signal waveform data.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
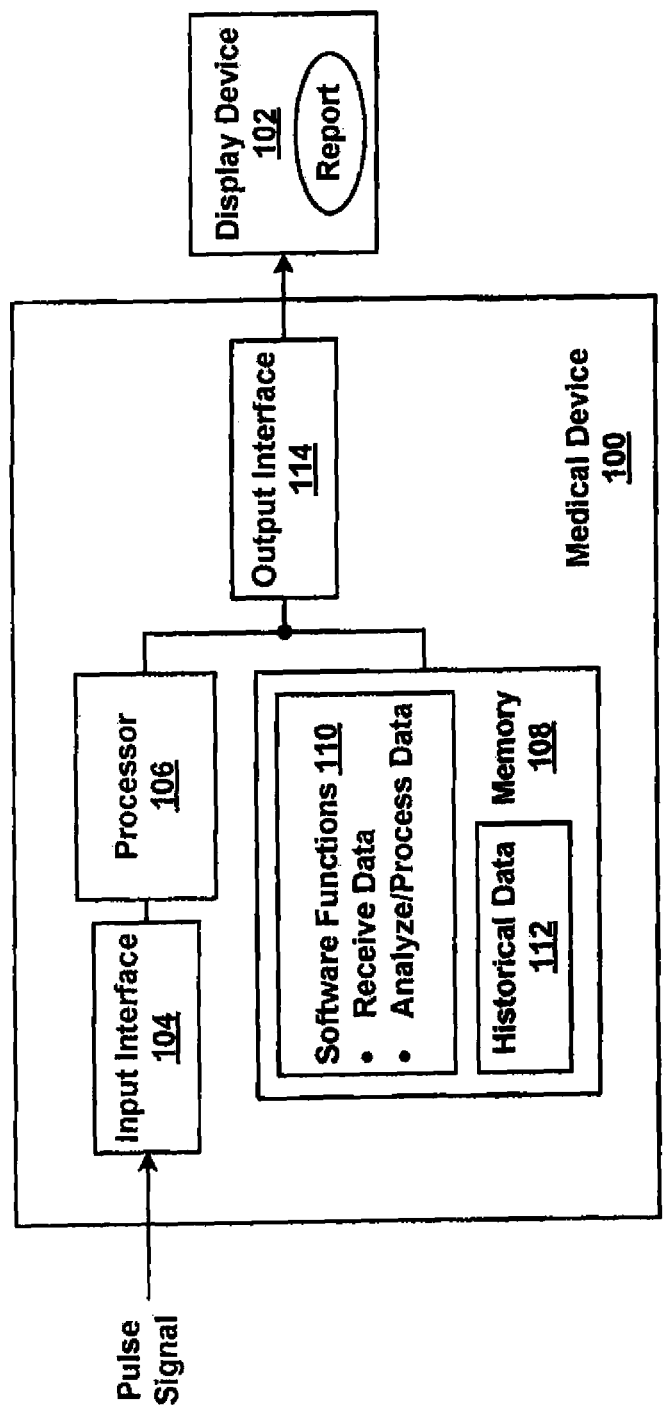
FIG. 1 shows an illustrative embodiment of a system for receiving and analyzing medical data.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Today's high stress induced lifestyle has raised a burden of non-communicable diseases globally, Diabetes mellitus (DM) is a metabolic disease contributing to high mortality and morbidity. According to International Diabetes Federation, incidences of DM in 2025 are projected to: rise by 195% in India, for example. Early diagnosis and management can prevent complications, and thus, save untimely deaths, and failure of vital organs like kidney, retina, heart and blood vessels, for example.

In example embodiments, systems and methods for diagnosis or prediction of Diabetes Mellitus (DM) are described. Diagnosis or prediction of DM may be performed by analyzing a pulse, and comparing the pulse with a morphology pattern that has been found to indicate a subject is suffering from DM. In one aspect, a pulse signal can be captured via wrist electrodes using bio-electric sensors based on an impedance plethysmographic principle, for example, and processed using feature extraction for diagnosis and assessment of the subject's proneness to DM. Analysis of the pulse signal and pulse morphology patterns provides an in-vitro, non-invasive, and low-cost method for diagnosing DM.

In addition, methods and systems in example embodiments can be used to analyze pulse types for diagnosis of other diseases. For example, a rhythm change may be specific to certain diseases (e.g., irregular pulse in atrial fibrillation), and other pulse patterns can be identified as being indicative of other diseases.

Referring now to the Figures, FIG. 1 is a system for receiving, and analyzing medical data. The system includes a medical device 100 that outputs to a display device 102. The medical device 100 includes an input interface 104 that receives medical readings from a patient and sends the medical readings to a processor 106. The medical readings may include pulse signal waveform data of a patient, for example. The pulse signal waveform data may be received continuously over time, or data representing a pulse signal over time may be received. The input interface 104 may also receive inputs from a user including instructions for processing the medical readings, for example. The processor 106 accesses memory 108 to execute any of the software functions 110 stored therein, such as to receive the medical readings analyze and process the readings, and to present data to the display device 102, for example. The processor 106 further accesses the memory 108 to retrieve stored historical data 112, or past medical results, personal health/medical data including family history data of a patient, anthropometry data of a patient, etc., and may combine the historical data 112 with the received medical readings to process the received medical readings. The processor 106 may output results to the display device 102 through an output interface 114. A system bus or an equivalent system may also be provided to enable communications between various elements of the medical device 100 and the display device 102, for example.

The medical device 100 generally can range from a handheld device, laptop, or personal computer to a larger computer such as a workstation and multiprocessor. The medical device 100 may also include an input device, such as a keyboard and/or a two or three-button mouse, if so desired. One skilled in the art of computer systems will understand that the example embodiments are not limited to any particular class or model of computer employed for the medical device 100 and will be able to select an appropriate system.

The medical device 100 can be attached to a bed/mattress/bedcover to record pulse recordings when the subject is relaxed, for example, to record resting heart rate pulse signals. In addition, the input interface 104 may be separate from the medical device 100, and may include any standard medical interface for collecting desired medical readings from a subject. For example, to collect pulse signals, the input interface 104 may include or connect to a wrist pulse signal device. The input interface 104 may connect to other pulse collection signal devices as well, such as those types that connect to other areas of the body like calf, toe, etc.

Further, the input interface 104 and the output interface 114 may be or include any standard computer interface and may include, for example, a keyboard, touchscreen display, etc. However, other interfaces may be used as well. Moreover, the memory 108 may include main memory and secondary storage. The main memory may include random access memory (RAM). Main memory can also include any additional or alternative memory device or memory circuitry. Secondary storage can be provided as well and may be persistent long term storage, such as read only memory (ROM), optical or magnetic disks, compact-disc read only memory (CD-ROM), or any other volatile or non-volatile storage systems. The memory 108 may include more software functions 110 as well, for example, executable by the processor 106 to record signals from a patient and interpret the signals as medical readings. The software functions 110 may be provided using machine language instructions or software with object-oriented instructions, such as the Java programming language. However, other programming languages (such as the C++ programming language for instance) could be used as well.

The processor 106 may operate according to an operating system, which may be any suitable commercially available embedded or disk-based operating system, or any proprietary operating, system. The processor 106 may comprise one or more smaller central processing units, including, for example, a programmable digital signal processing engine. The processor 106 may also be implemented as a single application specific integrated circuit (ASIC) to improve speed and to economize space.

It should be further understood that this and other arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

Figure 2:
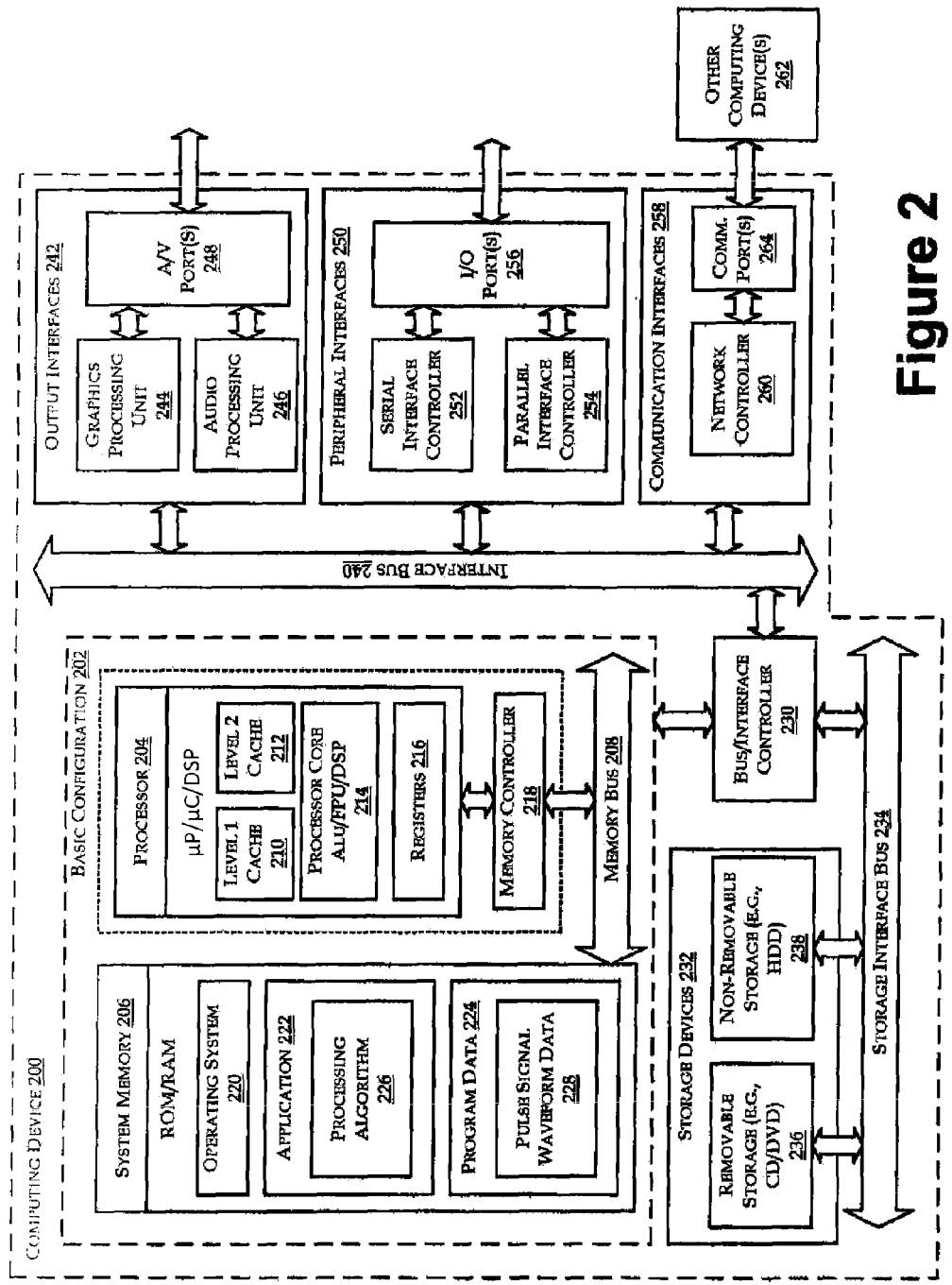
FIG. 2 shows an illustrative embodiment of a computing device arranged for receiving and analyzing medical data.

FIG. 2 is a block diagram illustrating another example computing device 200 arranged for receiving and analyzing medical data. In a very basic configuration 202, computing device 200 typically includes one or more processors 204 and system memory 206. A memory bus 208 can be used for communicating between the processor 204 and the system memory 206.

Depending on the desired configuration, processor 204 can be of any type including but not limited to a microprocessor (µP), a microcontroller (µC) a digital signal processor (DSP), or any combination thereof. Processor 204 can include one more, levels of caching, such as a level one cache 210 and a level two cache 212, a processor core 214, and registers 216. The processor core 214 can include air arithmetic logic unit (ALU), a floating point unit (FPU), a digital signal processing core (DSP Core), or any combination thereof. A memory controller 218 can also be used with the processor 204, or in some implementations the memory controller 218 can be an internal part of the processor 204.

Depending on the desired configuration, the system memory 206 can be of any type including but not limited to volatile memory (such as RAM), non-volatile memory (such as ROM, flag memory, etc.) or any combination thereof. System memory 206 typically includes an operating system 220, one or more applications 222, and program data 224. Application 222 includes algorithms 226 that may be arranged to perform any of the functions shown in FIGS. 3-4 described below, for example, depending on a configuration of the computing device, 200. Program Data 224 includes pulse signal waveform data 228 of a patient, for example. In some example embodiments, application 222 can be arranged to operate with program data 224 on the operating system 220. This described basic configuration is illustrated in FIG. 2 by those components within dashed line 202.

Computing device 200 can have additional features or functionality, and additional interfaces to facilitate communications between the basic configuration 202 and any required devices and interfaces. For example, a bus/interface controller 230 can be used to facilitate communications between the basic configuration 202 and one or more data storage devices 232 via a storage interface bus 234. The data storage devices 232 can be removable storage devices 236, non-removable storage devices 238, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media can include volatile and nonvolatile, removable and non-removable media implemented in any method or technology for storage of information, such as computer readable instructions, data structures, program modules, or other data.

System memory 206, removable storage 236 and non-removable storage 238 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 200. Any such computer storage media can be part of device 200.

Computing device 200 can also include an interface bus 240 for facilitating communication from various interface devices (e.g., output interfaces, peripheral interfaces, and communication interfaces) to the basic configuration 202 via the bus/interface controller 230. Example output interfaces 242 include a graphics processing unit 244 and an audio processing unit 246, which can be configured to communicate to various external devices such as a display or speakers via one or more A/V ports 248. Example peripheral interfaces 250 include a serial interface controller 252 or a parallel interface controller 254, which can be configured to communicate with external devices such as input devices (e.g., keyboard, mouse, pen, voice input device, touch input device, etc.) or other peripheral devices (e.g., printer, scanner, etc.) via one or more I/O ports 256. An example communication interface 258 includes a network controller 260, which can be arranged to facilitate communications with one or more other computing devices 262 over a network communication via one or more communication ports 264. The communication connection is one example of a communication media. Communication media may typically be embodied by computer readable instructions, data structures, program modules, or other data in a modulated data signal, and includes any information delivery media. A "modulated data signal" can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR) and other wireless media. In some examples, the term computer readable media as used herein can include storage media, communication media, or both.

Computing device 200 can be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 200 can also be implemented as a personal computer including both laptop computer and non-laptop computer configurations.

The medical device 100 in FIG. 1 or the computing device 200 in FIG. 2 may be configured to operate to receive a pulse signal and analyze the pulse signal to diagnose a disease, such as Diabetes Mellitus (DM). Diagnosis of DM may be performed by comparing the pulse signal with a morphology pattern that has been found to indicate a subject is suffering from DM, for example.

Figure 3:
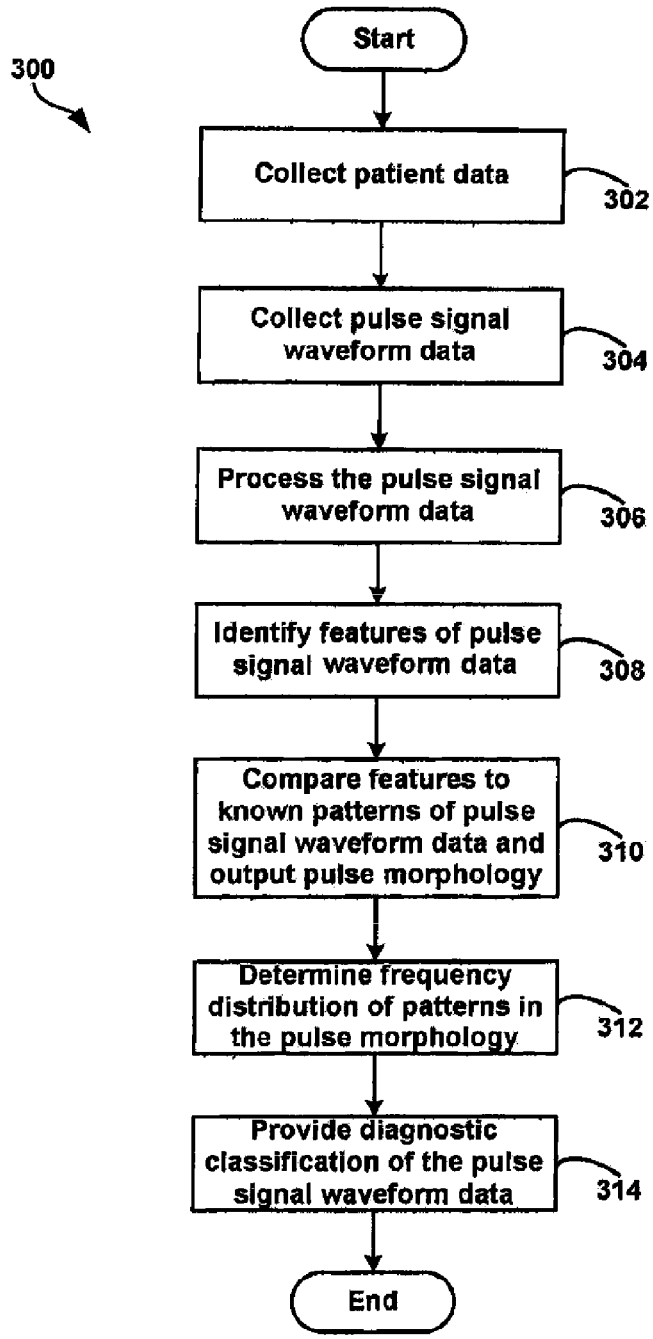
FIG. 3 shows a flowchart of an illustrative embodiment of a method for analyzing pulse signal waveform data to diagnose a disease.

FIG. 3 shows a flowchart of an illustrative embodiment of a method 200 for analyzing pulse signal waveform data to diagnose a disease. It should be understood that for this and other processes and methods disclosed herein, the flowchart shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. In addition, each block may represent circuitry that is wired to perform the specific logical functions in the process. Alternative implementations are included within the scope of the example embodiments of the present disclosure in which functions may be executed out of order from that shown or discussed, including substantially concurrent or in reverse order, depending on the functionality involved, as would be understood by those reasonably skilled in the art.

Initially, patient data is collected at block 302. Patient data may include test results of various clinical investigations including biochemistry (e.g., sugar), hematology, electrocardiogram, angiogram, lipids, x-ray and other relevant investigations, for example. In addition, patient data may include personal health or medical data of a patient, such as the patient's personal information, risk factors such as family history from maternal and paternal parents for diseases like Diabetes Mellitus, hypertension, ischaemic heart disease, or other metabolic diseases or conditions. Patient data may also include observed signs and symptoms of the patient or anthropometric data, such as height, weight, body mass index (BMI), and waist hip ratio, for example.

Following, pulse signal waveform data is collected at block 304. Pulse signal waveform data may be collected by recording Impedance phlebography, or impedance plethysmography (IPG) based pulse signal data as a function of time. The IPG-based pulse signal data may indicate small changes in electrical resistance of regions of the body that reflect blood volume changes. For example, pulse signals may be acquired or captured from a subjects wrist using bio-electric sensors. The pulse signals may be impedance plethysmographic pulse signals captured by using the bio-electric sensors. The collected pulse signals indicate a rate of change of impedance in a body segment, such as the wrist of the subject. Further, pulse signals may be collected over a period of time, such as for about five minutes, and may be configured into the pulse signal waveform data. The pulse signal waveform data may be periodic or substantially periodic, for example.

Pulse signals may be recorded over any period of time. In some examples, to obtain a number of patterns of pulse signal waveform data, a recording interval can be at least about one minute. Also, because the pulse signal waveform data is periodic, a long interval may not provide any additional information. An interval of about five minutes has been found to provide an effective and reliable amount of data. The interval may be reduced to about four minutes in good conditions (e.g., low noise, low disturbances) for some examples. However, the method 300 may be performed for pulse signal waveform data collected over any time interval. Results may be more accurate and reliable for an interval of about five minutes, for example.

Next, at block 306, the pulse signal waveform data is processed. In one example, the pulse signal waveform data can be further processed and converted to an ASCII format, for example. The pulse signal waveform data may be digitized to a binary format, which can then be decomposed into time series data that is stored in ASCII format. To do so, the binary data is input, and a first four bytes of data may represent a sample count. The sample count indicates, for example, a number of data points or records captured. Data can be stored in a sequence of two bytes, which are converted into a long number (e.g., a decimal number) that represents impedance at a time instance. Similarly, impedance can be calculated from the several sets of two bytes, and a rate of change of impedance can be determined and output over time as values separated by commas in a text file, for example, to output a pulse time series data file in ASCII format.

In another example, the pulse signal waveform data may be further processed to remove signal noise. For example, bandpass filtering is used for filtering undesired frequencies of the pulse signal waveform data to reduce background noise and optimize a signal-to-noise ratio. To remove signal noise, the pulse time series data file in ASCII format can be used. For a pulse signal waveform data collected over about five minutes, and sampled at a frequency of about 100 Hz, about 30,000 data points will be collected. A discrete Fourier transform can be performed on the 30,000 data points by applying a Fast Fourier Transform (FFT) algorithm to the data to decompose the data points into components of different frequencies, for example. Next, a power spectral density of the FFT decomposed data points can be, obtained, and frequencies at which a high signal power or high intensity is concentrated can be identified. A threshold value reflecting low signal power or low energy can be determined. A threshold filtering technique can be applied to the FFT decomposed data points to set FFT coefficients at frequencies that have less energy than the threshold value to zero. An inverse FFT (iFFT) can be applied to the modified FFT coefficients to provide a de-noised pulse signal waveform data.

Following, at block 308, features of the pulse signal waveform data are identified. Since the input data of the pulse signal waveform data may include about 30,000 data points, and because the pulse signal waveform data is substantially periodic, the data points may include repetitive or redundant information. Thus, the data points can be transformed into a reduced representation set of features that retain useful information, and redundant information can be discarded.

Because the pulse signal waveform data is substantially periodic, the pulse signal waveform data includes sub-waveforms or complexes. To identify features of the pulse signal waveform data, the complexes are extracted that are defined or identified by an on-set data point and an off-set data point of a corresponding sub-waveform in the pulse signal waveform data. Each complex may include a data point between the on-set and off-set data points that is a systolic peak corresponding to a heart beat. Improper peaks may be seen in the pulse signal waveform data, which can result in ectopic complexes. As a normal range for a rested heart rate is about 60-90 beats per minute, abnormal peaks occurring outside of a predetermined heart beat range can be interpreted as a pathology or ignored if the peaks are found as noise or interpreted as noise. In normal operation, few or no multiple, high amplitude peaks will be clustered together. However, in some instances, a peak may occur too soon after a previous peak (based on normal resting heart rates), or a peak may be missing in the instance of a missed heart beat or missed recording of the heart beat. For consideration of a pulse morphology, peaks occurring outside of an expected range, or missed peaks, can be ignored, but may be noted for instances of bradycardia or tachycardia conditions, for example.

Other features of each complex may be identified as well including data points preceding and following the systolic peak so as to characterize the complex. In addition, other features of data points may be identified, such as amplitude of a data point in the pulse signal waveform data, intervals between data points, and correlation among the data points. Mathematical relations (e.g., equal to, greater than, less than, etc.) between pairs of data points may also be obtained to characterize the pulse signal waveform data associated with each complex. Still further, other algebraic relationships amongst the data points can be obtained to uniquely characterize a pattern associated with each complex, for example.

Next, the identified features can be compared to known patterns of pulse signal waveform data and a pulse morphology is output, at block 310. For example, a database may include a number of known patterns of pulse signals in pulse signal waveform data, and corresponding features for each of the known patterns. The identified features of the pulse signal waveform data can be compared to the corresponding features for each of the known patterns to identify matches.

Depending on a number of features being compared, a number of matches may be identified. If an acceptable number of matches is found (e.g., the features can be approximately mapped onto an already existing pattern from the database), the pulse signal waveform data may be labeled by a label of the corresponding known pattern. If less than an acceptable number of matches is found, the pulse signal waveform data may be stored in the database as a new pattern with a new label. Data including the labels of patterns is output as the pulse morphology of the pulse signal waveform data.

Thus, a database of distinct pulse patterns observed in pulse signal waveform data can be constructed by populating the database with new patterns found in pulse signal waveform data, and features of the new patterns are given unique labels.

An acceptable number of matches may depend on the number of features being compared, and may be, for example, at least about a 50% to about a 75% or higher match rate. In addition, matches of features may occur if data points defining the features have magnitudes approximately the same or within a predetermined tolerance of each other. Alternatively, absolute values of the deflection points may not be compared, but rather, relations (e.g., less than, equal to, greater than) of the values of the deflection points are observed. Furthermore, because features of the pulse signal waveform data are seen over time, timing of the features or between the features may be matched as well with timing of features in the known patterns. To match a timing feature, the timing of a feature may be approximately the same or within a predetermined tolerance of each other.

In an alternate embodiment, instead of comparing the identified features to known patterns of pulse signal waveform data at block 310, the identified features of each complex may be used to construct a database of patterns as the patterns are observed in the pulse signal waveform data. A pattern is uniquely characterized by mathematical relations amongst features of data points, e.g., amplitudes of the data points. Once the database becomes populated with patterns, syntactical pattern recognition techniques can be used for pattern matching because there is a clear structure observed in the pulse morphology; for example.

Following, at block 312, a frequency distribution of patterns in the pulse morphology is determined. For example, a number of times each different pattern appears in the pulse morphology is determined. A table may be prepared including a number of times each different pattern appears in the pulse morphology.

A diagnostic classification of the pulse signal waveform data is then provided at block 314. Pulse signals captured during an interval of five minutes may display different morphology patterns corresponding to different complexes. For diagnostic classification, a most dominant pattern appearing in the pulse morphology over the specified interval (e.g., the pattern appearing with the most frequency) can be identified, and a label of the most dominant pattern is determined. The label may indicate a specific disease that is characterized by a patient that has a specific pulse signal waveform data.

Alternatively, after identifying the most dominant pattern, the most dominant pattern may be compared with pulse patterns classified as being indicative of a specific disease. In one example, the most dominant pattern may be compared with pulse patterns classified as being indicative of Diabetes Mellitus or Metabolic Syndrome (e.g., a combination of medical disorders that increase a risk of developing cardiovascular disease and diabetes).

In addition, because impedance plethysmography is a technique for detecting blood vessel occlusion that determines volumetric changes in the limb, other disorders or diseases affecting vascular/cardiovascular health can be diagnosed using the method 300. Example disorders that may be diagnosed using the method 300 include cardiovascular heart disease, ischaemic heart disease, atherosclerosis, angina, stroke, cerebrovascular disease, congestive heart failure, coronary artery disease, myocardial infarction, or peripheral vascular disease. To diagnose any of these diseases a particular pulse pattern characterizing or being indicative of the disease is established and compared with the most dominant pattern appearing in the pulse signal waveform data. To generate or identify characterizing patterns, blind, observational studies are performed involving, healthy subjects as well as patients suffering from the earmarked disease and patients suffering from other diseases, for example.

Figure 4:
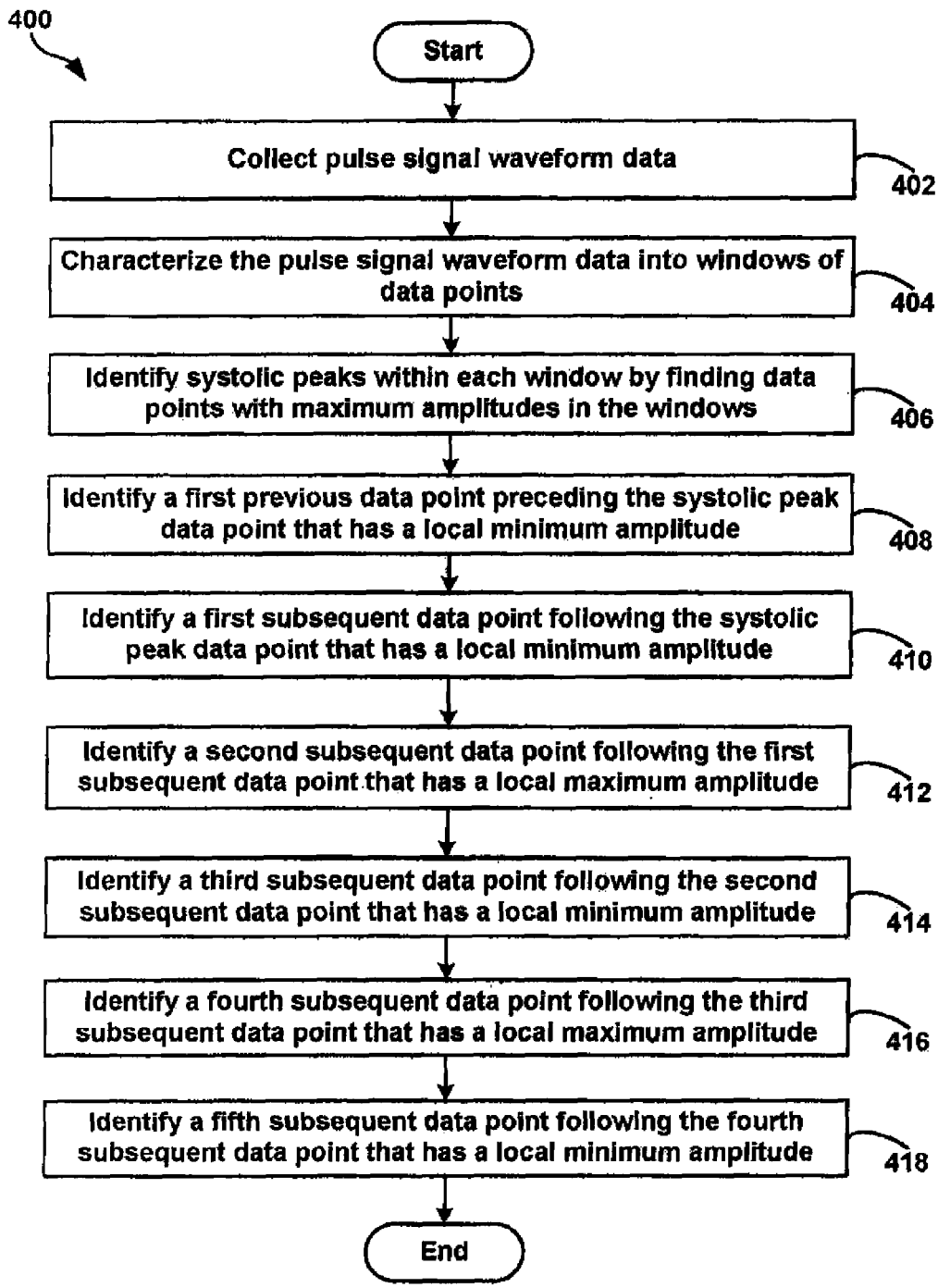
FIG. 4 shows a flowchart of an illustrative embodiment of another method for analyzing pulse signal waveform data.
Figure 5:
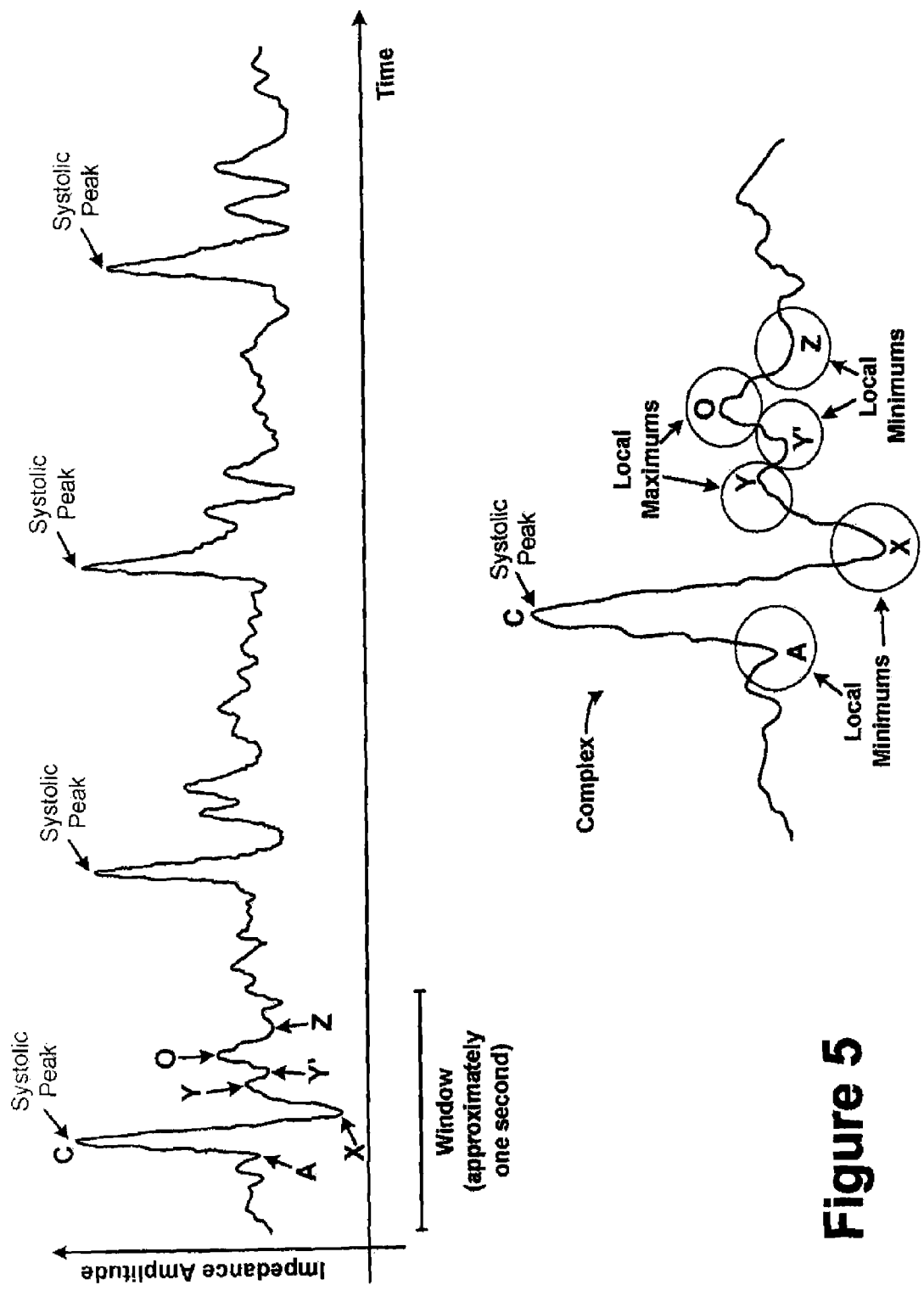
FIG. 5 shows an illustrative embodiment of pulse signal waveform data.

FIG. 4 shows a flowchart of an illustrative embodiment of another method 400 for analyzing pulse signal waveform data, and FIG. 5 show an example pulse signal waveform data. Initially, pulse signal waveform data is collected at block 402. For example, a series of pulse signal waveform, data may be collected over time. Following, the pulse signal waveform data is characterized into windows of data points at block 404. The windows may be referred to as complexes. The pulse signal waveform data may be collected over a time period of about five minutes, and data may be collected at a sampling frequency of about 100 Hz to collect a total of about 30,000 data points. A window may include about 100 data points or be equivalent to about one second, for example. A size of a window may be chosen based on a patient's resting heart rate. For example, a normal lower boundary value of a resting heart rate is about 60 beats per minute, or about one beat per second. Thus, within a window size of one second, the heart will beat about once. Thus, within each complex, about one systolic peak will appear.

In the pulse signal waveform data shown in the graph of FIG. 5, the data is graphed over about 4 seconds of time during which the heart beat is seen about 4 times giving rise to 4 systolic peak data points. Thus, next at block 406, systolic peaks are identified within each window by finding data points with maximum amplitudes in the windows of about 100 data points over the entire pulse signal waveform data of about a 300 second interval, for example. The data points representing the systolic peaks are given a unique label, such as "C" in FIG. 5. Spurious peaks in the complexes that would indicate a resting heart rate beyond the range of about 60 to about 100 beats per minute can be ignored, for example.

Following, deflection data points surrounding the systolic peak data points are identified. For example, a first previous data point preceding the systolic peak data point that has a local minimum amplitude is identified at block 408. The first previous data point is given a label, such as "A" in FIG. 5. The first preceding data point may be referred to as the on-set data point referring to the on-set of a systolic peak. As shown in FIG. 5, to identify the on-set data point "A", an algorithm is performed to identify a local minimum prior to the systolic peak "C" data point. Amplitudes of data points preceding the systolic peak "C" are compared to one another until the local minimum is identified (e.g., until a rate of change of the line graph begins to change). Or, for example, amplitudes of data points are compared until a change is found that would indicate a local minimum (such as a change from a decreasing amplitude to an increasing amplitude in neighboring data points).

Following, deflection points following or subsequent to the systolic peak C are identified. For example, a next deflection point is identified by finding a first subsequent data point following the systolic peak data point that has a local minimum amplitude at block 410. The first subsequent data point is given a label, such as "X" in FIG. 5.

Next, a second subsequent data point following the first subsequent data point that has a local maximum amplitude is identified at block 412. The second subsequent data point is given, a label, such as "Y" in FIG. 5. To find a local maximum, similar algorithms are performed as to find a local minimum, such as to compare amplitudes of data points until a change is found that would indicate a local maximum (such as a change from an increasing amplitude to a decreasing amplitude in neighboring data points).

Next, a third subsequent data point following the second subsequent data point that has a local minimum amplitude is identified at block 414. The third subsequent data point is given a label, such as Y' in FIG. 5. Next, a fourth subsequent data point following the third subsequent data point that has a local maximum amplitude is identified at block 416. The fourth subsequent data point is given a label, such as "O" in FIG. 5. Last, a fifth subsequent data point following the fourth subsequent data point that has a local minimum amplitude is identified at block 418. The fifth subsequent data point is given a label, such "Z" in FIG. 5. The data point Z is referred to as the off-set data point indicating an end of the window, for example.

As seen in FIG. 5, a sub-waveform from data points A to Z is referred to as complex. Since the pulse signal waveform data is periodic, these complexes repeat throughout the five minute recording interval, for example. Data points A are the on-set data points and data points Z are the off-set data points of the sub-waveforms in the various complexes, and data points A, C, X, Y, Y', O and Z are the deflection points in each of the complexes.

In example embodiments, using the methods of FIGS. 3 and 4, pulse morphology pattern recognition can be performed, and a diagnostic classification can be provided to indicate if a subject suffers from a disease. Data regarding physiological variables, clinical investigations, and family history, etc., can also be captured for validation of the diagnostic classification. The methods 300 and 400 for diagnostic classification are in-vitro, non-invasive and low-cost, for example.

Experimental studies were performed to evaluate the methods 300 and 400. Data was collected at multiple centers using healthy volunteers, diabetic patients, and non-diabetic patients that suffered from other metabolic diseases, such as ischemic heart disease (IHD). Tables 1 and 2 below indicate the different centers, patients, and corresponding diseases of the patients. Note that a patient may have been suffering from more than one disease/disorder. Hence, although a total number of patients studied was 316, the total number of cases studied was 394.

TABLE 1

Center-wise Cases

| Centers | Volunteers | No. of Volunteers |
|---|---|---|
| Hospital A | Patients | 106 |
| Hospital B | Patients | 71 |
| Clinic | Patients | 74 |
| Foundation | Patients | 37 |
| Diabetic Camp | Patients | 28 |
| College of Arts & Science | Healthy | 53 |
| Engineering College | Healthy | 46 |
| CDAC | Healthy | 81 |
| Others (Health Dept., etc.) | Healthy | 61 |
| Total | | 557 |

TABLE 2

Disease-wise Cases

| Disease | No. of patients |
|---|---|
| IHD | 87 |
| Dyslipidemia + Other Heart Diseases | 21 |
| Hypertension | 82 |
| Diabetes Mellitus | 91 |
| Asthma & Other Respiratory Diseases | 22 |
| Arthritis + Musculoskeletal | 27 |
| Gastroenterological | 43 |
| Nephrological | 7 |
| Neurological | 6 |
| Cancer | 4 |
| Anaemia | 4 |
| Total | 394 |

Initially, for each subject, multidimensional data was collected. The dimensions of the data included 1) medical family history from maternal and paternal sides, 2) personal health/medical record including sex and age data, 3) clinical investigations of the subject such as blood pressure, glucose level (fasting & PP), lipid profile, and hemogram, 4) pulse related parameters such as strength, volume, depth, pulse rate, etc., 5) anthropometry data such, as height and weight, and 6) impedance plethysmographic pulse signal recorded for a period of about 300 seconds at a sampling frequency of about 100 Hz.

Clinical data was procured and high frequency noise was filtered. The data was processed in a series of steps including those described above in FIGS. 3 and 4. For example, the processing included (1) signal acquisition along with filtering, (2) data conversion from proprietary binary format to ASCII format, (3) data transformation for further processing including identifying various deflection points, complexes, and classification of the complexes into "dominant" and "nondominant" (ectopic) types, (4) pulse waveform recognition to identify onset and offset of diagnostic waves and major deflection points, (5) feature extraction measuring amplitudes and intervals, and (6) diagnostic classification.

The pulse signal waveform data is captured and studied in the time domain. Each complex is identified by the on-set data points in the pulse signal waveform data. In each complex, seven major deflection points (A, C, X, Y, Y', O, Z) are identified using the method 400 described above. FIGS. 6-9 illustrate example pulse morphology patterns that were generally observed. Each pattern is uniquely recognized by correlations amongst the deflection points of the pulse waveform.

Figure 6:
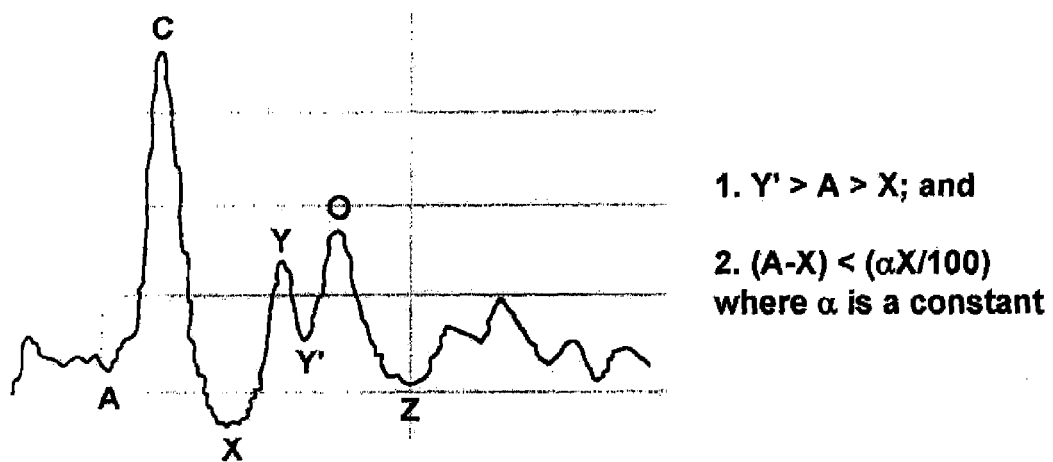
FIGS. 6-10 show illustrative embodiments of portions of pulse signal waveform data with data points labeled.

For example, in FIG. 6, a complex is shown that has values of deflection points that substantially follow the relationships shown in Equations (1) and (2) below.

$$Y' > A > X \quad \text{Equation (1)}$$

$$(A - X) < \left(\frac{\alpha X}{100}\right), \text{ where } \alpha \text{ is a constant} \quad \text{Equation (2)}$$

An example value of α is about 80. For example, a value of the deflection point A may have a value greater than the value of the deflection point X, but the difference between the two values should not be too large.

Figure 7:
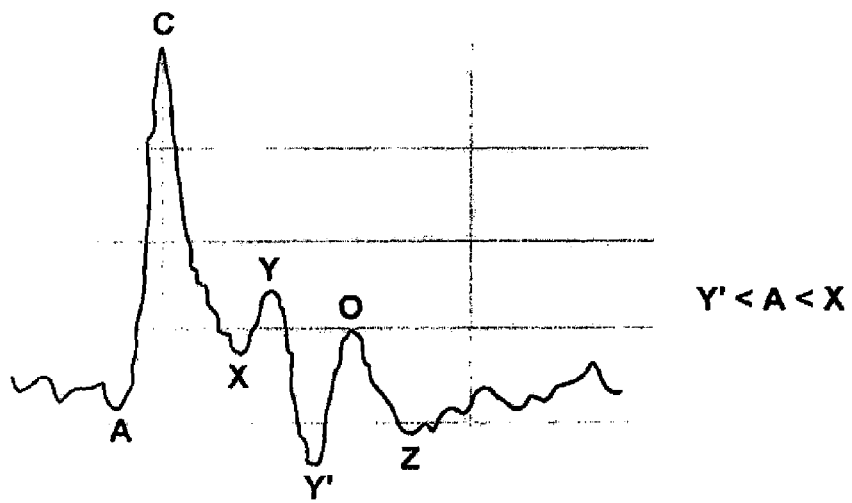

The complex shown in FIG. 7 has values of deflection points that substantially follow the relationship shown in Equation (3).

$$Y' < A < X \quad \text{Equation (3)}$$

Figure 8:
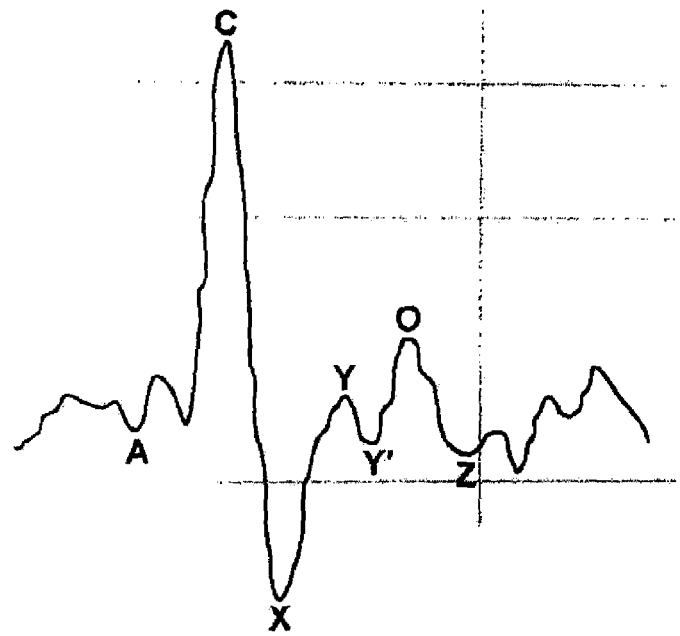

The complex shown in FIG. 8 has values of deflection points that substantially follow the relationships shown in Equations (4) and (5).

$$X < \min\{A, Y'\} \quad \text{Equation (4)}$$

$$(A - X) > \left(\frac{\alpha X}{100}\right), \text{ where } \alpha \text{ is a constant} \quad \text{Equation (5)}$$

Figure 9:
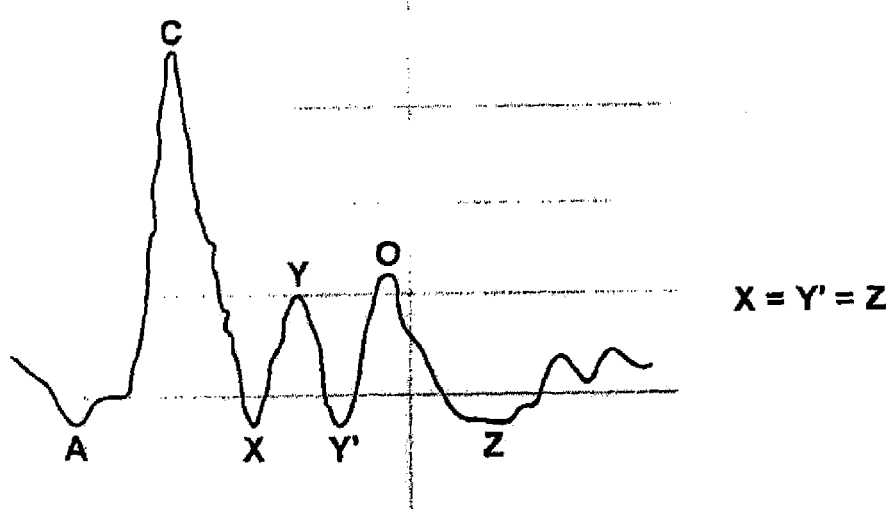

The complex shown in FIG. 9 has values of deflection points that substantially follow the relationship shown in Equation (6).

$$X = Y' = Z \quad \text{Equation (6).}$$

The patterns shown in FIGS. 6-9 may, be stored in a database and used during pulse morphology creation or generation (e.g., in method 300).

Figure 10:
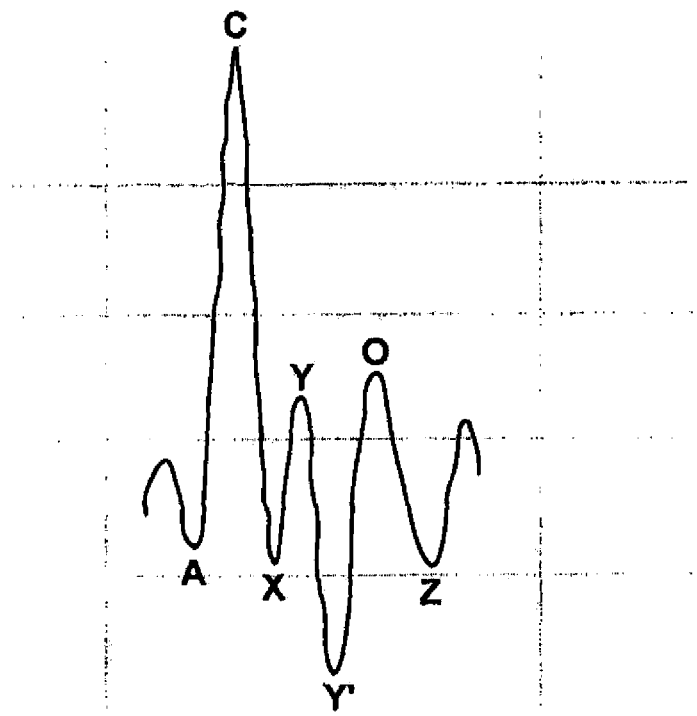

FIG. 10 illustrates an example complex that has values of deflection points that substantially follow the relationship shown in Equation (7).

$$A \geq X > Y' \quad \text{Equation (7)}$$

The complex shown in FIG. 10, including deflections points that follow the relationship in Equation (7) has been classified to be indicative of diabetes mellitus (DM).

In each of Equations (1)-(7), the relationships may still be considered satisfied if the values of the deflection data points substantially follow the relationships in the Equations within a tolerance level. For example, Equation (7) may be considered to be satisfied if X is greater than A by the tolerance level.

Accuracy of the pulse morphology pattern classified to be indicative of DM was about 98.74%. Dominance of a pulse morphology pattern as shown in FIG. 10 in the pulse morphology of the Impedance Plethysmographic pulse signal waveform data captured over a period of about five minutes was used as an identifier to diagnose a subject as diabetic. Table 3 below summarizes results of the experimental study.

TABLE 3

| Health Status | No. of Volunteers | Exceptions Found | Remarks |
|---|---|---|---|
| Healthy | 241 | 2 | Of 241, only 2 healthy subjects had a pulse pattern indicating DM. Of 225 non-diabetic patients, only 5 subjects had pulse pattern indicating DM. |
| Patients: | 316 | 5 | |
| Diabetic | 91 | | |
| Non-diabetic | 225 | | |
| Total | 557 | 7 | |

Accuracy of the hypothesis: 98.7423%

Figure 11:
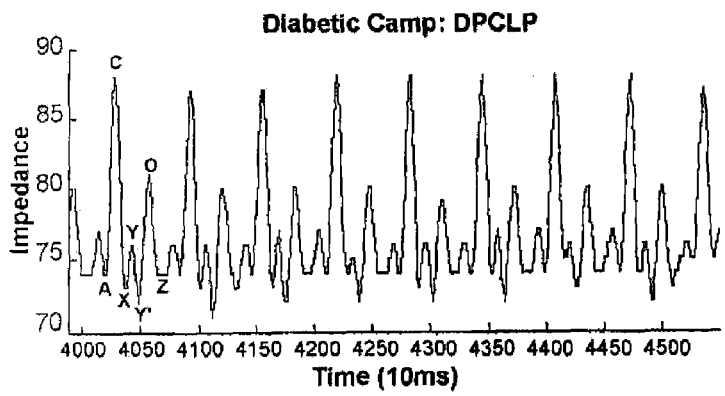
FIGS. 11-22 show illustrative embodiments of portions of pulse signal waveform data from diabetic patients.
Figure 12:
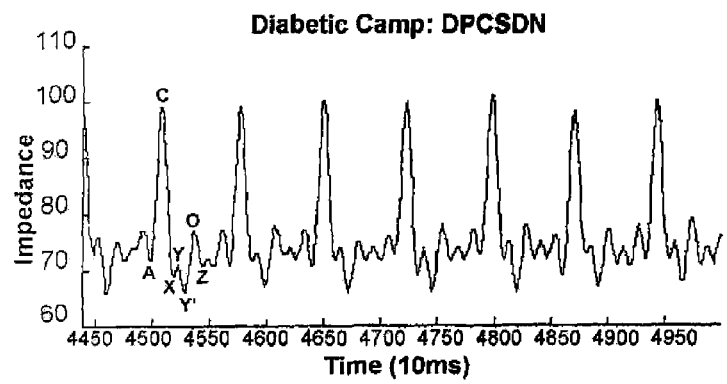
Figure 13:
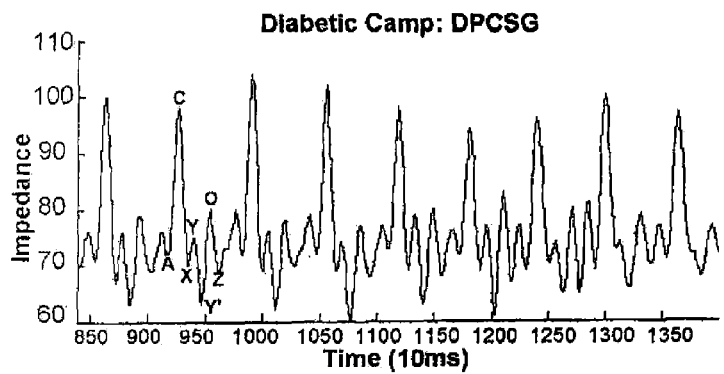
Figure 14:
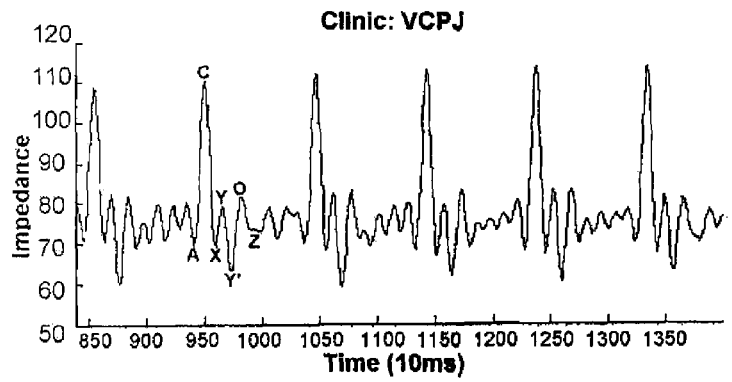
Figure 15:
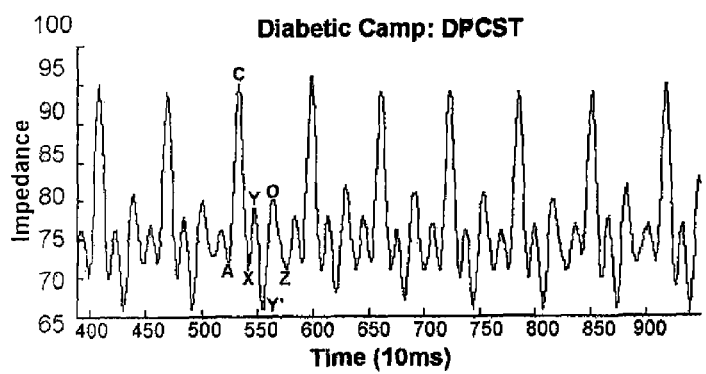
Figure 16:
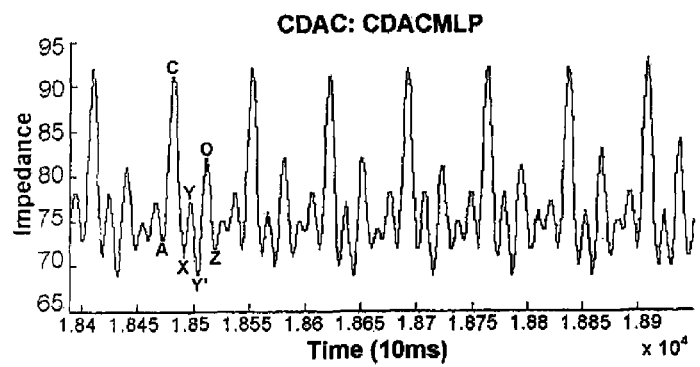
Figure 17:
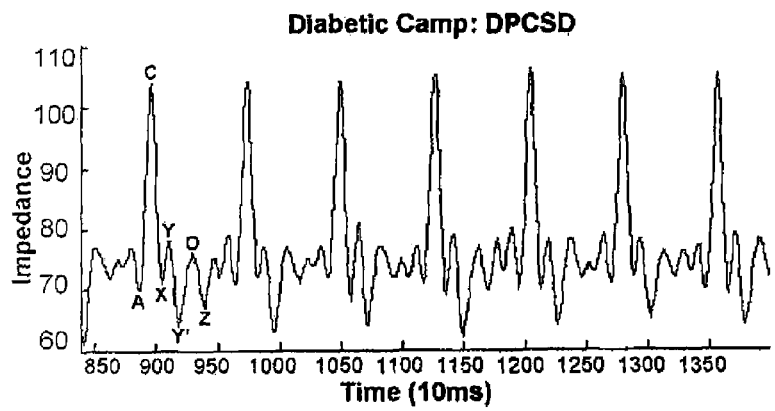

FIGS. 11-22 illustrate pulse signal waveform, data from diabetic patients. In FIG. 11, the patient had blood sugar levels of (fasting) F-118 and (postprandial) PP-130. In FIG. 12, the patient had blood sugar levels of F-130 and PP-148. In FIG. 13, the patient had blood sugar levels of F-137 and PP-187. In FIG. 14, the patient had blood sugar levels of F-134 and PP-287. In FIG. 15, the patient had blood sugar levels of F-130 and PP-210. In FIG. 16, the patient had blood sugar levels of F-134 and PP-200. In FIG. 17, the patient had blood sugar levels of F-144 and PP-200.

Figure 18:
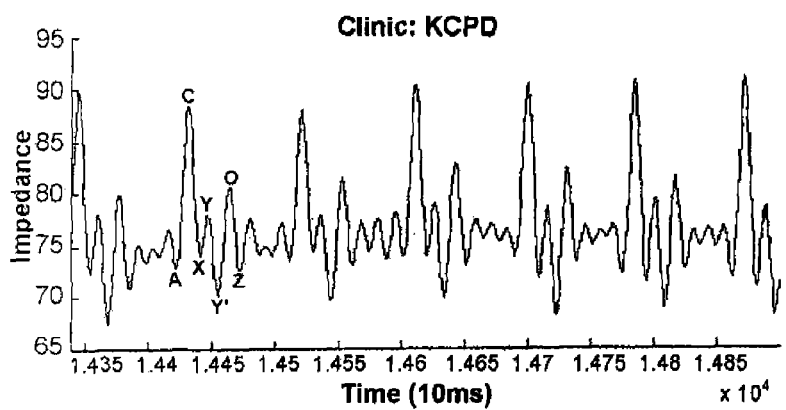
Figure 19:
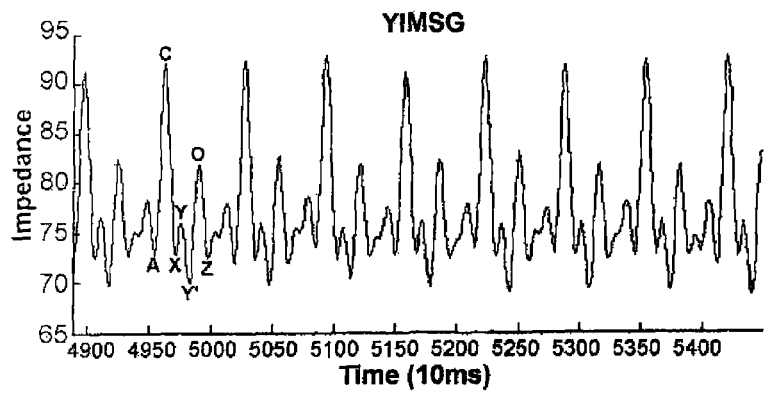
Figure 20:
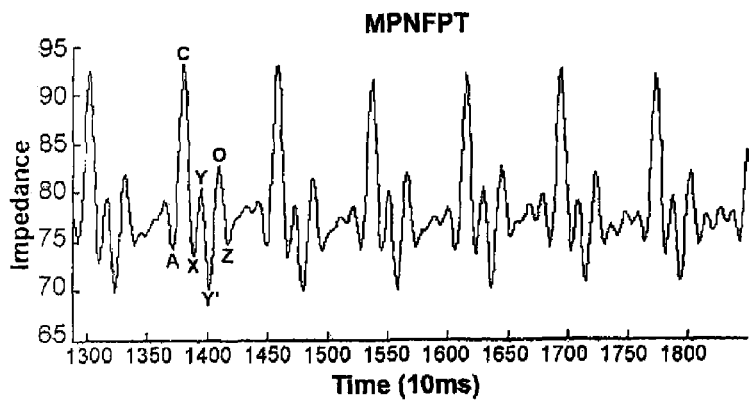
Figure 21:
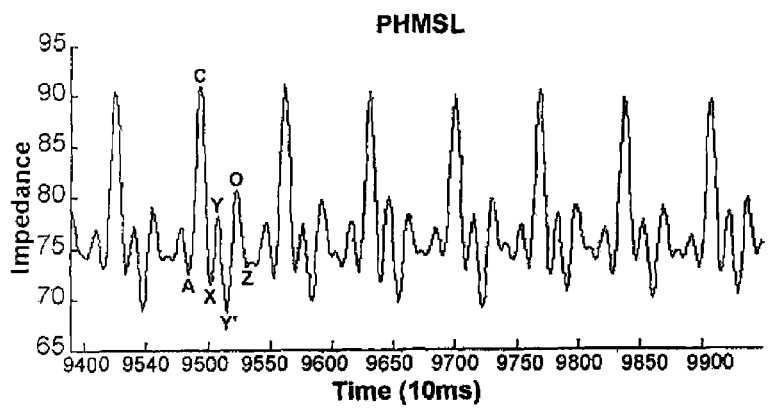
Figure 22:
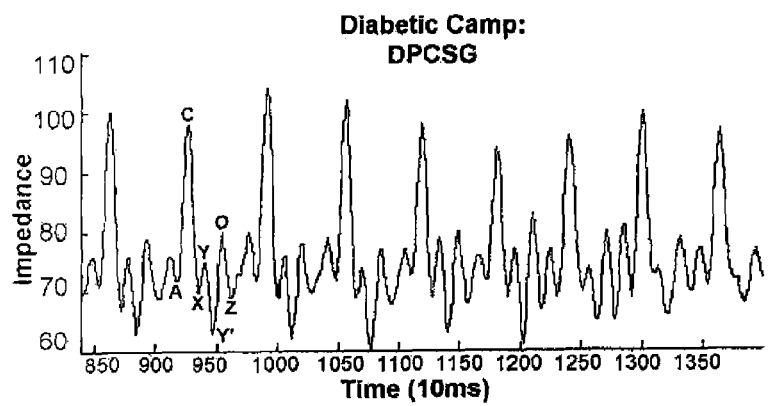
Figure 23:
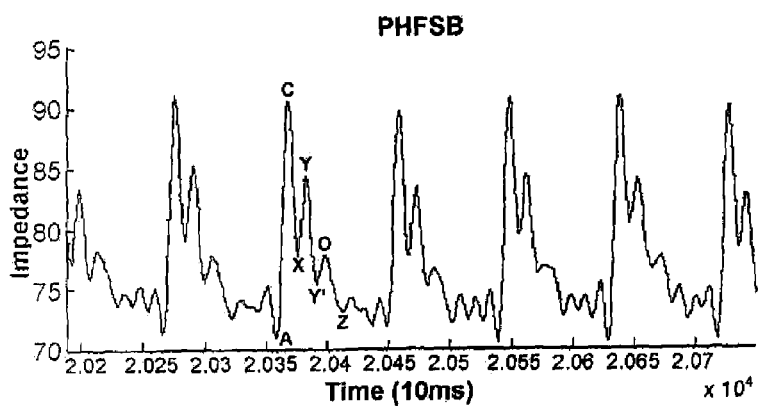
FIGS. 23-28 show illustrative embodiments of portions of pulse signal waveform data from non-diabetic subjects (e.g., either healthy subjects or subjects suffering from other diseases).
Figure 24:
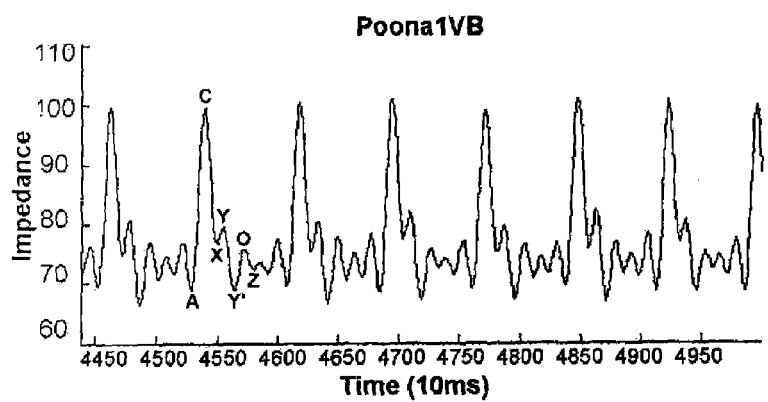
Figure 25:
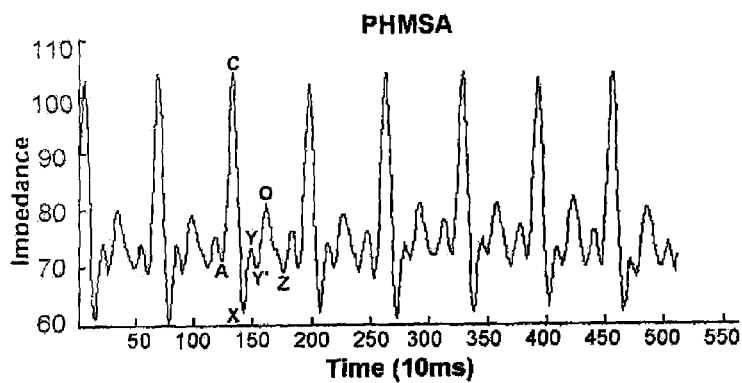
Figure 26:
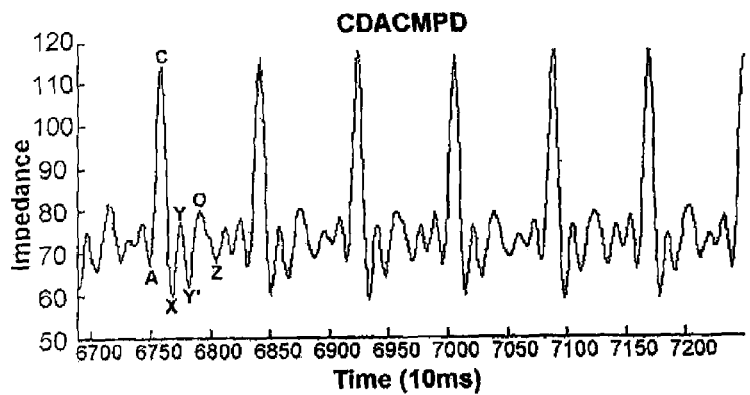
Figure 27:
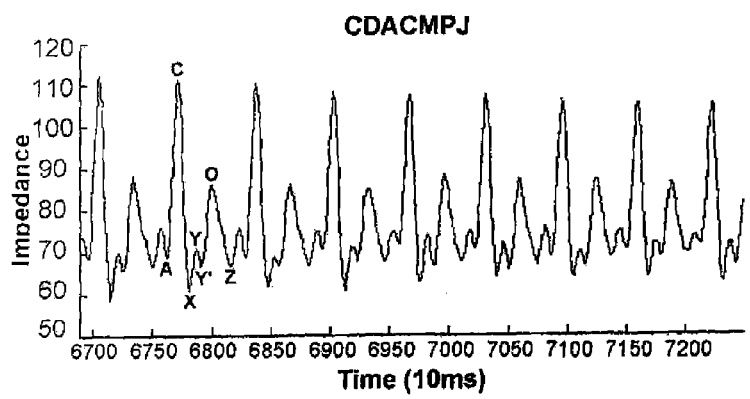
Figure 28:
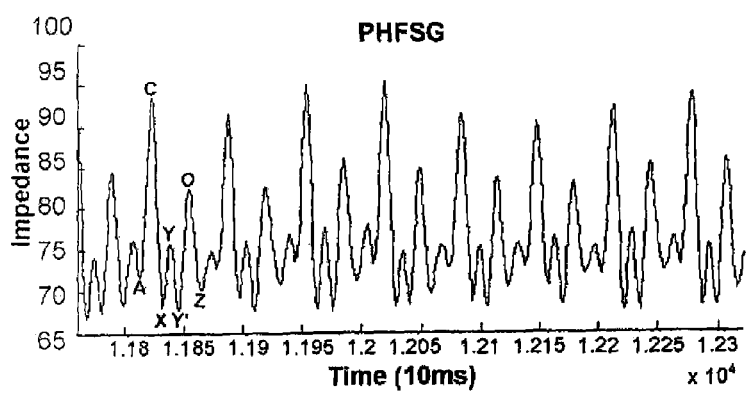

As seen in FIGS. 11-22, each of the pulse signal waveform data satisfies the relationship (A≥X>Y') of Equation (7). In FIGS. 17-18, however, X is slightly greater than A, but within an acceptable tolerance level, for example.

FIGS. 23-28 illustrate pulse signal, waveform data from non-diabetic subjects (e.g., either healthy patients or patients suffering from other diseases). In FIGS. 23-28, the pulse signal waveform data generally does not satisfy the relationship (A≥X>Y') of Equation (7).

Hyperglycemia induced vascular changes in diabetic patients can lead to several complications such as retinopathy, nephropathy, and neuropathies. Using example methods described herein, pulse examination and classification of an impedance plethysmographic pulse morphology pattern for DM can enable early detection of DM or other hyperglycemia induced vascular changes.

In example embodiments, methods may be performed by patients at home and minimize a need for time consuming visits to pathological laboratories, for example. Early detection of diseases such as DM can enable early corrective measures in diet and lifestyle and proper treatment for reducing morbidity and mortality caused directly or indirectly by DM, for example.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The present disclosure is not to be limited in terms of the particular embodiments described in this disclosure, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an"

should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together; A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual Member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-1 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of making diagnostic classifications of pulse signal waveform data, the method comprising:
receiving, at a processor, pulse signal waveform data;
identifying, by the processor, systolic peak data points in the pulse signal waveform data corresponding to a systolic peak indicating a heartbeat;
based on the systolic peak data points, identifying, by the processor, complexes in the pulse signal waveform data, wherein a complex comprises a sub-waveform in the pulse signal waveform data approximately between an on-set data point and an off-set data point, wherein the on-set data point is a data point preceding a given systolic peak data point that has a local minimum amplitude and the off-set data point is a data point subsequent to the given systolic peak that has a local minimum amplitude, and wherein each complex includes deflection data points between the on-set point and the off-set point, wherein one of the deflection data points is a systolic peak corresponding to a heartbeat;
determining, by the processor, a pattern distribution of the complexes based on relative magnitudes of at least three deflection data points of the complexes, wherein the pattern distribution indicates a frequency of pulse patterns appearing in the complexes of the pulse signal waveform data; and
based on the pattern distribution, making, by the processor, a diagnostic classification of the pulse signal waveform data;
wherein making the diagnostic classification of the pulse signal waveform data comprises determining a relationship between a first previous data point preceding the systolic peak, a first subsequent data point following the systolic peak, and a third subsequent data point following the systolic peak and a second subsequent data point;
wherein making the diagnostic classification of the pulse signal waveform data comprises determining that the pulse signal waveform data is indicative of Diabetes Mellitus when the following relationship is substantially satisfied:

$$A \geq X > Y',$$

where A is the first previous data point preceding the systolic peak, X is the first subsequent data point following the systolic peak, and Y' is the third subsequent data point following the systolic peak and the second subsequent data point.

2. The method of claim 1, wherein making the diagnostic classification of the pulse signal waveform data comprises determining that the pulse signal waveform data is indicative of Diabetes Mellitus or Hyperglycemia induced vascular changes.

3. The method of claim 1, further comprising for each complex determining the deflection data points by:
identifying the first previous data point preceding the systolic peak data point that has a local minimum amplitude, the first preceding data point being the on-set data point;
identifying the first subsequent data point following the systolic peak data point that has a local minimum amplitude;
identifying the second subsequent data point following the first subsequent data point that has a local maximum amplitude;
identifying the third subsequent data point following the second subsequent data point that has a local minimum amplitude;
identifying a fourth subsequent data point following the third subsequent data point that has a local maximum amplitude; and
identifying a fifth subsequent data point following the fourth subsequent data point that has a local minimum amplitude, the fifth subsequent data point being the off-set data point.

4. The method of claim 1, further comprising receiving personal health and medical data of a patient from which the pulse signal waveform data was recorded, and based on the personal health and medical data of the patient, making the diagnostic classification of the pulse signal waveform data.

5. The method of claim 1, further comprising converting the pulse signal waveform data into time series data that is stored in ASCII format.

6. The method of claim 5, further comprising filtering the pulse signal waveform data by:
- performing a discrete Fourier transform on the time series data to decompose data points into components of different frequencies;
- determining a power spectral density of the decomposed data points;
- identifying frequencies at which a signal power is concentrated;
- based on the identified frequencies, determining a threshold value reflecting low signal power;
- setting decomposed data points at frequencies that have less signal power than the threshold value to zero to provide modified data points; and
- performing an inverse fast Fourier transform (iFFT) to the modified data points to output de-noised pulse signal waveform data.

7. The method of claim 1, further comprising identifying systolic peaks corresponding to heart beats in each complex by identifying a data point in each complex having a maximum amplitude.

8. The method of claim 1, further comprising based on relationships between the deflection data points, characterizing each complex in the pulse signal waveform data.

9. The method of claim 1, further comprising identifying within the pattern distribution of complexes a pattern appearing most frequently in the pulse signal waveform data.

10. The method of claim 9, further comprising comparing the pattern appearing most frequently in the pulse signal waveform data with a pattern classified as being indicative of a disease.

11. The method of claim 1, further comprising comparing deflection data points of patterns of complexes within the pattern distribution of complexes with deflection data points in known patterns of pulse signals to identify matches.

12. The method of claim 11, further comprising when deflection data points of a given pattern of a complex do not sufficiently match with deflection data points in any of the known patterns of pulse signals, populating a database of distinct pulse signal patterns observed in pulse signal waveform data with the given pattern.

13. The method of claim 1, wherein receiving pulse signal waveform data comprises receiving Impedance phlebography/impedance plethysmography based pulse signal data as a function of time.

14. The method of claim 1, wherein receiving pulse signal waveform data comprises receiving pulse signal waveform data collected over a time period, and wherein a time interval of the sub-waveform in the pulse signal waveform data is selected based on a patient's resting heart rate so that approximately one systolic peak indicating the heart beat occurs during the time interval of the sub-waveform.

15. A non-transitory computer readable medium having stored therein instructions executable by a computing device to cause the computing device to perform functions of:
- receiving pulse signal waveform data;
- identifying systolic peak data points in the pulse signal waveform data corresponding to a systolic peak indicating a heartbeat;
- based on the systolic peak data points, identifying complexes in the pulse signal waveform data, wherein a complex comprises a sub-waveform in the pulse signal waveform data approximately between an on-set data point and an off-set data point, wherein the on-set data point is a data point preceding a given systolic peak data point that has a local minimum amplitude and the off-set data point is a data point subsequent to the given systolic peak that has a local minimum amplitude, and wherein each complex includes deflection data points between the on-set point and the off-set point, wherein one of the deflection data points is a systolic peak corresponding to a heartbeat;
- determining a pattern distribution of the complexes based on relative magnitudes of at least three deflection data points of the complexes, wherein the pattern distribution indicates a frequency of pulse patterns appearing in the complexes of the pulse signal waveform data; and
- based on the pattern distribution, making a diagnostic classification of the pulse signal waveform data;
- wherein making the diagnostic classification of the pulse signal waveform data comprises determining a relationship between a first previous data point preceding the systolic peak, a first subsequent data point following the systolic peak, and a third subsequent data point following the systolic peak and a second subsequent data point;
- wherein making the diagnostic classification of the pulse signal waveform data comprises determining that the pulse signal waveform data is indicative of Diabetes Mellitus when the following relationship is substantially satisfied:

$$A \geq X > Y',$$

where A is the first previous data point, X is the first subsequent data point, and Y' is the third subsequent data point.

16. The non-transitory computer readable medium of claim 15, wherein the functions further include determining that the pulse signal waveform data is indicative of Diabetes Mellitus.

17. A non-transitory computer readable medium having stored therein instructions executable by a computing device to cause the computing device to perform functions of:
- receiving pulse signal waveform data;
- identifying systolic peak data points in the pulse signal waveform data corresponding to a systolic peak indicating a heartbeat;
- based on the systolic peak data points, identifying complexes in the pulse signal waveform data, wherein a complex comprises a sub-waveform in the pulse signal waveform data approximately between an on-set data point and an off-set data point, wherein the on-set data point is a data point preceding a given systolic peak data point that has a local minimum amplitude and the off-set data point is a data point subsequent to the given systolic peak that has a local minimum amplitude, and wherein each complex includes deflection data points between the on-set point and the off-set point, wherein one of the deflection data points is a systolic peak corresponding to a heartbeat;
- identifying a first previous data point preceding the systolic peak data point that has a local minimum amplitude, the first preceding data point being the on-set data point;
- identifying a first subsequent data point following the systolic peak data point that has a local minimum amplitude;

identifying a second subsequent data point following the first subsequent data point that has a local maximum amplitude;

identifying a third subsequent data point following the second subsequent data point that has a local minimum amplitude;

identifying a fourth subsequent data point following the third subsequent data point that has a local maximum amplitude; and identifying a fifth subsequent data point following the fourth subsequent data point that has a local minimum amplitude, the fifth subsequent data point being the off-set data point, determining a pattern distribution of the complexes based on relative magnitudes of at least three deflection data points of the complexes, wherein the pattern distribution indicates a frequency of pulse patterns appearing in the complexes of the pulse signal waveform data; and based on the pattern distribution, making a diagnostic classification of the pulse signal waveform data;

wherein making the diagnostic classification of the pulse signal waveform data comprises determining that the pulse signal waveform data is indicative of Diabetes Mellitus when the following relationship is substantially satisfied:

$$A > X > Y',$$

where A is the first previous data point, X is the first subsequent data point, and Y' is the third subsequent data point.

18. The non-transitory computer readable medium of claim 15, wherein the functions further include:

identifying within the pattern distribution of complexes a pattern appearing most frequently in the pulse signal waveform data; and comparing the pattern appearing most frequently in the pulse signal waveform data with a pattern classified as being indicative of a disease.

19. A system comprising:

a database storing known patterns of pulse signals;

an input interface for receiving pulse signal waveform data; and a processor configured to identify systolic peak data points in the pulse signal waveform data corresponding to a systolic peak indicating a heartbeat, the processor further based on the systolic peak data points configured to identify complexes in the pulse signal waveform data, wherein a complex comprises a sub-waveform in the pulse signal waveform data approximately between an on-set data point and an off-set data point, wherein the on-set data point is a data point preceding a given systolic peak data point that has a local minimum amplitude and the off-set data point is a data point subsequent to the given systolic peak that has a local minimum amplitude, and wherein each complex includes deflection data points between the on-set point and the off-set point, wherein one of the deflection data points is a systolic peak corresponding to a heartbeat, wherein based on relative magnitudes of at least three deflection data points of the complexes, the processor is configured to compare a pattern of each complex with the known patterns of pulse signals in the database, and to make a diagnostic classification of the pulse signal waveform data;

wherein making the diagnostic classification of the pulse signal waveform data comprises determining a relationship between a first previous data point preceding the systolic peak, a first subsequent data point following the systolic peak, and a third subsequent data point following the systolic peak and a second subsequent data point;

wherein making the diagnostic classification of the pulse signal waveform data comprises determining that the pulse signal waveform data is indicative of Diabetes Mellitus when the following relationship is substantially satisfied:

$$A \geq X > Y',$$

where A is the first previous data point, X is the first subsequent data point, and Y' is the third subsequent data point.

* * * * *

UNITED STATES PATENT AND TRADEMARK OFFICE
CERTIFICATE OF CORRECTION

| | | |
|---|---|---|
| PATENT NO. | : 9,220,437 B2 | Page 1 of 2 |
| APPLICATION NO. | : 13/256568 | |
| DATED | : December 29, 2015 | |
| INVENTOR(S) | : Dhurandhar et al. | |

It is certified that error appears in the above-identified patent and that said Letters Patent is hereby corrected as shown below:

IN THE SPECIFICATION

In Column 1, Line 5, delete "APPLICATION" and insert -- APPLICATIONS --, therefor.

In Column 1, Line 8, delete "371" and insert -- § 371 --, therefor.

In Column 1, Line 32, delete "pulse' examination" and insert -- pulse examination --, therefor.

In Column 1, Line 45, delete "time;" and insert -- time, --, therefor.

In Column 2, Line 17, delete "receiving, pulse" and insert -- receiving pulse --, therefor.

In Column 3, Line 27, delete "globally," and insert -- globally. --, therefor.

In Column 3, Line 30, delete "to: rise" and insert -- to rise --, therefor.

In Column 3, Lines 53-54, delete "receiving," and insert -- receiving --, therefor.

In Column 3, Line 66, delete "readings analyze" and insert -- readings, analyze --, therefor.

In Column 4, Line 55, delete "operating, system." and insert -- operating system. --, therefor.

In Column 5, Line 16, delete "more," and insert -- more --, therefor.

In Column 5, Line 18, delete "air" and insert -- an --, therefor.

In Column 5, Line 27, delete "flag memory," and insert -- flash memory, --, therefor.

In Column 5, Line 33, delete "computing device," and insert -- computing device --, therefor.

Signed and Sealed this
Twelfth Day of April, 2016

Michelle K. Lee
*Director of the United States Patent and Trademark Office*

IN THE SPECIFICATION

In Column 7, Line 24, delete "subjects wrist" and insert -- subject's wrist --, therefor.

In Column 8, Line 8, delete "points can be," and insert -- points can be --, therefor.

In Column 8, Line 14, delete "PET (iFFT)" and insert -- FFT (iFFT) --, therefor.

In Column 8, Line 39, delete "multiple," and insert -- multiple --, therefor.

In Column 9, Line 17, delete "being, compared," and insert -- being compared, --, therefor.

In Column 9, Line 41, delete "morphology;" and insert -- morphology, --, therefor.

In Column 10, Line 12, delete "involving," and insert -- involving --, therefor.

In Column 10, Line 19, delete "waveform," and insert -- waveform --, therefor.

In Column 8, Line 15, delete "PET" and insert -- FFT --, therefor.

In Column 11, Line 4, delete "given," and insert -- given --, therefor.

In Column 11, Line 21, delete "such "Z"" and insert -- such as "Z" --, therefor.

In Column 11, Line 25, delete "as complex." and insert -- as a complex. --, therefor.

In Column 11, Line 49, delete "eases" and insert -- cases --, therefor.

In Column 12, Line 25, delete "such," and insert -- such --, therefor.

In Column 13, Line 16, delete "may, be" and insert -- may be --, therefor.

In Column 13, Line 51, delete "waveform," and insert -- waveform --, therefor.

In Column 13, Line 65, delete "signal, waveform" and insert -- signal waveform --, therefor.

In Column 15, Line 15, delete "together;" and insert -- together, --, therefor.

In Column 15, Line 34, delete "Member" and insert -- member --, therefor.

In Column 15, Line 51, delete "1-1 cells" and insert -- 1-3 cells --, therefor.